(12) United States Patent
Abbott et al.

(10) Patent No.: US 7,947,500 B2
(45) Date of Patent: May 24, 2011

(54) LIQUID CRYSTALLINE SUBSTRATES FOR CULTURING CELLS

(75) Inventors: Nicholas L. Abbott, Madison, WI (US); Jeffrey C. Mohr, Madison, WI (US); Christopher J. Murphy, Madison, WI (US); Elise Huang, Fitchburg, WI (US); Juan J. DePablo, Madison, WI (US); Nathan A. Lockwood, Minneapolis, MN (US); Sean P. Palecek, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/777,320

(22) Filed: May 11, 2010

(65) Prior Publication Data

US 2010/0221834 A1    Sep. 2, 2010

Related U.S. Application Data

(62) Division of application No. 11/565,363, filed on Nov. 30, 2006, now Pat. No. 7,732,152.

(60) Provisional application No. 60/740,944, filed on Nov. 30, 2005.

(51) Int. Cl.
*G01N 33/53* (2006.01)
*G01N 33/567* (2006.01)
*G01N 33/566* (2006.01)
*C12N 5/00* (2006.01)
*C12N 5/02* (2006.01)

(52) U.S. Cl. ......... 435/395; 435/7.2; 435/325; 435/408; 435/7.21; 436/501

(58) Field of Classification Search ................. 435/7.21, 435/395
See application file for complete search history.

(56) References Cited

FOREIGN PATENT DOCUMENTS
WO    2005/010160 A2    2/2005

OTHER PUBLICATIONS

Brake et al., "Biomolecular interactions at phospholipid-decorated surfaces of liquid crystals" 2003 Science 302:2094-2097.
Geiger et al., "Transmembrane crosstalk between the extracellular matrix—cytoskeleton crosstalk" 2001 Nature Reviews 2:793-805.
Balaban et al., "Force and focal adhesion assembly: a close relationship studied using elastic micropatterned substrates" 2001 Nature Cell Biology 3:466-472.
International Search Report mailed Oct. 15, 2007 for PCT/US2006/061414; Wisconsin Alumni Research Foundation.
Yan-Yeung Luk et al., "Non-Toxic Thermotropic Liquid Crystals for Use With Mammalian Cells" 2004 Liquid Crystals Taylor and Francis, Abingdon, GB vol. 31 No. 5 pp. 611-621.
Li-Lin Cheng et al., "Compatibility of Lyotropic Liquid Crystals with Viruses and Mammalian Cells that Support the Replication of Viruses" 2005 Biomaterials p. 7173-7182.
Besseau et al., "Production of Ordered Collagen Matrices for Three-Dimensional Cell Culture" Biomaterials vol. 23 No. 1 pp. 27-36, 2007.

*Primary Examiner* — Valarie Bertoglio
(74) *Attorney, Agent, or Firm* — Quarles & Brady LLP (57) ABSTRACT

The present invention is directed to liquid crystalline substrates useful in the culture of cells and methods of their use. In certain embodiments, the invention provides methods and devices for imaging changes (e.g., reorganization) of extracellular matrix components by living cells.

5 Claims, 5 Drawing Sheets

LIQUID CRYSTALLINE SUBSTRATES FOR CULTURING CELLS

CROSS REFERENCE TO RELATED APPLICATION

This application is a divisional application of U.S. application Ser. No. 11/565,363, filed on Nov. 30, 2006, allowed as U.S. Pat. No. 7,732,152, which claims the benefit of U.S. Provisional Application No. 60/740,944, filed Nov. 30, 2005, both of which are incorporated by reference herein in their entirety.

STATEMENT REGARDING FEDERALLY SPONSORED RESEARCH

This invention was made with United States government support awarded by the National Science Foundation—Grant No. DMR-0079983. The United States has certain rights in this invention.

FIELD OF THE INVENTION

This invention relates generally to liquid crystal technology. More particularly, the present invention is directed to liquid crystalline substrates for culturing cells and related methods.

BACKGROUND OF THE INVENTION

The functions of cells in biological systems are guided by the spatial and temporal delivery of a range of chemical and mechanical cues. A wide variety of engineered materials have been investigated with the goal of exerting control over cell behaviors such as adhesion to surfaces, differentiation, and proliferation in in vitro and biomedical applications. The interactions of cells with solid surfaces, for example, have been engineered by controlling surface chemistry, topographical features, compliance of the substrate, and combinations of these parameters. Synthetic materials have also formed the basis of approaches that measure the interactions between cells and their environments. For example, certain approaches have previously been described that use microfabricated elastomeric posts to measure the patterns of mechanical forces exerted by cells on surfaces.

The liquid crystalline state is widely encountered in biological systems. For example, the membranes of cells are liquid crystalline, and concentrated solutions of biomolecules such as DNA and proteins are known to form liquid crystals. In light of this, it is surprising that few studies aimed at engineering synthetic materials to interact with live cells have explored the use of synthetic liquid crystals. Past studies have investigated the orientations of the nematic liquid crystal 4'-pentyl-4-cyanobiphenyl (5CB) on cells attached to surfaces. These cells, however, were fixed (i.e., dead) and the liquid crystal used in their investigation (5CB) has subsequently been shown to cause cell death when contacted with live cells for short periods of time. In a separate study, Luk and coworkers surveyed liquid crystalline materials containing a variety of functional groups and found several liquid crystals that were non-toxic to live mammalian cells. In particular, fluorinated liquid crystals exhibited minimal toxicity toward 3T3 fibroblasts and corneal epithelial cells.

Accordingly, there exists a need in the field to engineer synthetic materials that, in a first aspect, offer a suitable culture substrate for living cells and, in a second aspect, provide means to monitor cell behaviors such as adhesion to surfaces, differentiation, and proliferation.

SUMMARY OF THE INVENTION

In a first embodiment, the present invention is directed to methods for culturing cells on a cell culture substrate. Such methods include steps of: (a) providing a cell culture substrate by: (i) preparing an interface between an aqueous phase and a liquid crystalline phase; and (ii) depositing a protein or peptide layer at the interface; (b) seeding living cells onto the protein or peptide layer; and (c) culturing the living cells on the cell culture substrate.

In a preferred embodiment, the protein layer comprises at least one protein or peptide that is an extracellular matrix component and, in particularly preferred embodiments, the extracellular matrix component is collagen, gelatin, laminin, or elastin. Alternatively, or in addition, the protein or peptide layer may comprise synthetic peptides and proteins such as, e.g., polylysine.

In certain embodiments, the proteins and peptides are deposited at the interface from cell culture media. In other embodiments, the proteins or peptides of the protein layer are further incorporated into polyelectrolyte multilayer films deposited at the interface.

The liquid crystal is substantially non-toxic to living cells and can be a low molecular weight liquid crystal, a polymeric liquid crystal, a composite material containing a liquid crystal or a liquid crystalline elastomeric material.

The present invention is further directed to methods for detecting cell-induced changes to a cell culture substrate by living cells. Such methods include steps of: (a) providing a cell culture substrate by: (i) preparing an interface between an aqueous phase and a liquid crystalline phase; and (ii) depositing a protein or peptide layer at the interface; (b) seeding living cells onto the protein or peptide layer of the cell culture substrate; (c) maintaining the living cells under culture conditions; and (d) detecting reorganization of the liquid crystalline phase. The reorganization indicates cell-induced changes between the living cells and the cell culture substrate. In a particularly preferred embodiment, the living cells are human embryonic stem cells and the method provides for visualizing developmental changes occurring in the cultured cells.

The invention also encompasses cell culture substrates that include: (a) an aqueous phase; (b) a liquid crystalline phase wherein an interface is formed between the aqueous phase and liquid crystalline phase; and (c) a protein or peptide layer positioned at the interface. In preferred embodiments, the protein or peptide layer comprises at least one protein or peptide that is an extracellular matrix component and, in preferred embodiments, the protein layer includes collagen, gelatin, laminin, or elastin. Alternatively, or in addition, the protein layer may comprise a synthetic polypeptide or a naturally occurring peptide or protein. In certain embodiments, the proteins or peptides of the protein layer are further incorporated into a polyelectrolyte multilayer film deposited at the interface. The liquid crystal is substantially non-toxic to living cells and can be a low molecular weight liquid crystal, a polymeric liquid crystal, a composite material containing a liquid crystal or a liquid crystalline elastomeric material.

In yet another aspect, the invention provides a device for detecting cell-induced changes to a cell culture substrate by living cells, comprising: (a) a cell culture substrate having: (i) an aqueous phase; (ii) a liquid crystalline phase wherein an interface is formed between the aqueous phase and liquid crystalline phase; and (iii) a protein or peptide layer positioned at the interface; and (b) a means for imaging reorganization of the liquid crystalline phase. Reorganization indicates changes to the cell culture substrate induced by cells cultured on the cell culture substrate.

Other objects, features and advantages of the present invention will become apparent after review of the specification, claims and drawings.

BRIEF DESCRIPTION OF THE DRAWINGS

FIG. 1. A) Schematic illustration of the geometry for producing interfaces between aqueous phases and immiscible thermotropic liquid crystals. Note that the thicknesses of the slide, grid, and Matrigel film are not to scale. The Matrigel thickness indicated is based on the thickness of a dried Matrigel film on glass (~10 nm). Dashed lines in the TL205 liquid crystalline film represent an example of the director profile for planar anchoring. B) The liquid crystal TL205 is a proprietary mixture of cyclohexane-fluorinated biphenyls and fluorinated terphenyls; representative chemical structures are shown. C) Fluorescence image of TL205 following exposure to a FITC-labeled Matrigel solution for 2 h under conditions leading to gelation. D-F) Optical images (crossed polars) of TL205 after 2 h in contact with phosphate buffer (D), a solution of Matrigel under conditions leading to gelation (E), or a 1 µM solution of bovine serum albumin (F). Scale bars are 100 µm.

FIG. 3. A-B) Optical images (crossed polars) of TL205 in contact with cell medium for four days with (A) and without (B) a layer of Matrigel at the aqueous-TL205 interface. C) Optical image (crossed polars) of TL205 after 3 h in contact with a 100 µM suspension of 2DLPC liposomes in PBS. D) Optical image (crossed polars) of TL205 after 30 min in contact with a mixture of 100 µM DLPC and 1 µM BSA in PBS. Scale bars are 100 µm.

DETAILED DESCRIPTION OF THE INVENTION

I In General

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

Synthetic liquid crystals possess a number of properties that may make them useful when engineering interfaces to live cells. First, liquid crystals are anisotropic elastic fluids with splay, bend and twist elastic constants often on the order of 1 pN. The values of these elastic constants can be manipulated substantially by changes in the structure of the molecules comprising the liquid crystals. Consequently, these materials can reorganize under the influence of stresses comparable in magnitude to those transmitted from cells to their environments, thus potential providing a facile manner for reporting mechanical interaction of cells and their environments. The orientational order of liquid crystals near interfaces (the "anchoring" of the liquid crystal) is known to be highly sensitive to the nature of the interactions between the mesogens forming the liquid crystal and a confining interface. For example, the orientation of liquid crystals has been shown to be coupled to the presence and organization of phospholipids and proteins adsorbed at aqueous-liquid crystal interfaces. The orientation of liquid crystals are also dependent on the chemical structure of interfaces that they contact and thus changes in chemical structure or organization of molecules induced for example by enzymes that are secreted by cells can also be reported by liquid crystals.

The present invention provides liquid crystal-based substrates on which cells may be cultured. Such substrates may be incorporated into devices that measure and detect cell-induced changes in a cell culture substrate (e.g., a protein layer) by living cells cultured on the substrate. Such methods involve the deposition of a thin film of a peptide or protein layer (e.g., Matrigel) on the surface of a thermotropic liquid crystal, and the seeding of the cells on the decorated liquid crystal. It is possible to use the crystals to image the mechanical reorganization of protein or peptides by living cells. As well, the present invention provides certain methods and devices that permit facile observation of the reorganization of the extracellular matrix of cells. The invention also permits measurement of the mechanical forces transmitted by cells to surfaces.

Accordingly, in a first aspect the invention provides methods for culturing cells on a liquid crystalline-based cell culture substrate. Such methods include steps of: (a) providing a cell culture substrate by: (i) preparing an interface between an aqueous phase and a liquid crystalline phase; and (ii) depositing a protein or peptide layer at the interface; (b) seeding living cells onto the protein or peptide layer; and (c) culturing the living cells on the cell culture substrate.

The protein layer preferably includes at least one protein or peptide that is or may function as an extracellular matrix component such as, but not limited to, gelatin, laminin or collagen. The material available under the tradename Matrigel is a particularly preferred composition for use as the protein layer. Matrigel has demonstrated particular utility in this invention for the culture of human embryonic stem cells. However, the protein layer may, alternatively or in addition, comprise a synthetic polypeptide such as, e.g., polylysine.

Figure 1:
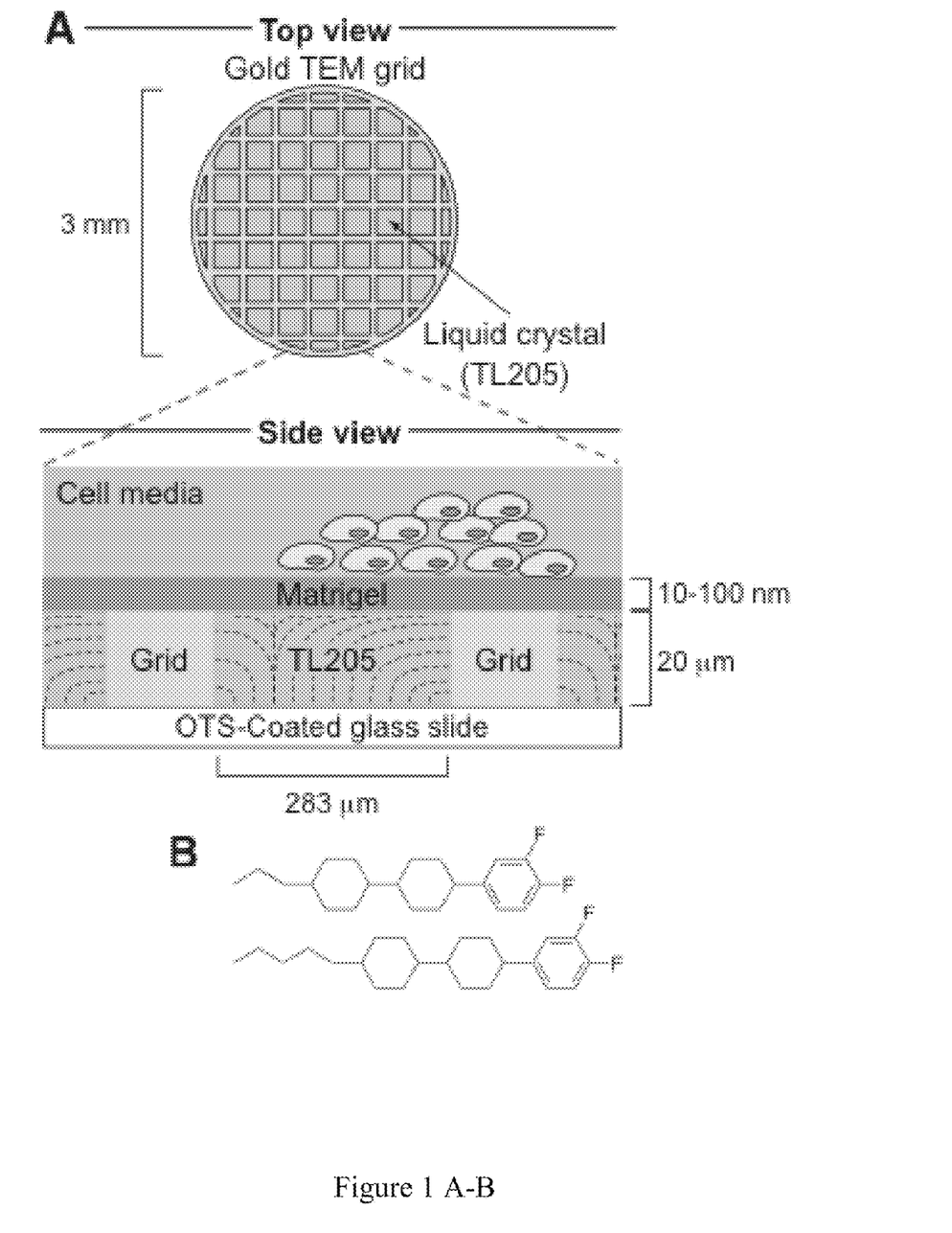

One specific embodiment described herein utilizes an approximately planar interface between the nematic liquid crystal TL205 (a proprietary mixture of cyclohexane-fluorinated biphenyls and fluorinated terphenyls) and an aqueous solution or cell media (FIG. 1A-B). The use of the approximately planar interface is not a limitation of the invention, and the invention includes interfaces that are not planar. In particular, the invention includes droplets of liquid crystals that will form curved interfaces with aqueous phases. In the described example, the approximately planar interfaces were prepared by hosting the TL205 in a gold TEM grid, which stabilizes the aqueous-TL205 interface. This geometry permits easy observation and interpretation of the orientations of the liquid crystals at the aqueous-TL205 interface and permits exchange of the aqueous phase or cell media.

The term "liquid crystal", as used herein, refers to an organic composition in an intermediate or mesomorphic state between solid and liquid. Suitable liquid crystals for use in the present invention include, but are not limited to, thermotropic liquid crystals that are substantially nontoxic to living cells. The term "substantially non-toxic" refers to compositions that exhibit little or no toxicity with respect to living cells, particularly eukaryotic cells, and most preferably mammal cells. Such compositions include liquid crystals with chemical functional groups such as fluorine atoms, fluorophenyl groups, or difluorophenyl groups. Preferred such liquid crystals include C series liquid crystals, TL205 and cholesterics, and substantially non-toxic liquid crystals can be identified by measurements of cytotoxicity, using the methods and criteria reported by Luk and coworkers in Luk, Y. Y.; Campbell, S. F.; Abbott, N. L.; Murphy, C. J. "Non-Toxic Thermotropic Liquid Crystals for Use with Mammalian Cells", *Liquid Crystals,* 31, 611 (2004).

The invention is not limited to the non-toxic liquid crystals specifically identified by Luk and coworkers. It may employ polymeric liquid crystals, composite materials comprising particles and liquid crystals, or polymers and liquid crystals, as well as elastomeric liquid crystals. A preferred liquid crystalline elastomer is synthesized from the mesogen M4OCH3 and polymethylhydrosiloxane, according to A. Komp and coworkers "A versatile preparation route for thin free standing liquid single crystal elastomers" *Macromol. Rapid Commun,* 26: 813-818, 2005. Other LC elastomers suitable for use in the current invention are described by Deng in "Advances in liquid crystal elastomers", *Progress in Chemistry,* 18 (10): 1352-1360, 2006, and references cited therein. The scope of the invention also includes use of liquid crystalline hydrogels, as described by Weiss, F. and Finkelmann H. in *Macromolecules;* 37(17); 6587-6595, 2004, and references cited therein. Other embodiments use a composite comprising a dispersion of solid particulates, such as but not limited to microspheres, mixed with liquid crystal. Such composites are known by those skilled in the art to form a gel.

Furthermore, the invention is not limited to the non-toxic liquid crystals identified by Luk and coworkers. It is anticipated that in some cases, the presence of the protein substrate or other adsorbed/deposited layer on the liquid crystal will lower the toxicity of liquid crystals to cells. For example, plasma treatment of the surface of a liquid crystalline elastomer can be used to lower the toxicity of the liquid crystal.

A distinctive feature of this system is that the liquid crystal layer is in direct contact with the peptide or protein layer (e.g., the composition available under the tradename Matrigel), which in turn is in contact with the cells. As cells grow, differentiate, migrate, invade matrices, change shape, and undergo other changes of state, they impart subtle structural changes to the protein or peptide layer. These changes are amplified and transduced by the liquid crystals, which become an effective readout. Matrigel is the trade name for a gelatinous protein mixture secreted by mouse tumor cells and currently available from BD Biosciences. This mixture resembles the complex extracellular environment found in many tissues and is used by cell biologists as a substrate for cell culture. However, there are many alternatives to Matrigel for use in the present invention. Alternatives include other proteins commonly found in the extracellular matrix of cells, including laminins, collagens, gelatin and other modified extracellular matrix proteins. The current invention also anticipates the use of synthetic or semisynthetic peptide-containing layers where the peptide sequence leads to interactions with the cell such as attachment of the cells to the layers. These layers, protein and semisynthetic, can be deposited at the interface of the liquid crystals using a variety of methods, including physical adsorption from solution, gelation and adsorption from solution, incorporation into multilayer structures formed at the interface such as polyelectrolyte multilayer (PEM) films, incorporation into amphiphilic molecules such as peptide amphiphiles, and covalent attachment to the liquid crystal. An example of a synthetic peptide sequence that can be used with the present invention is polylysine.

PEM films are particularly advantageous in that agents may be incorporated into their multilayer design such that the agent may be delivered to the local environment of the cultured cells at predetermined times and/or conditions. For example, a certain chemokine may be incorporated into a degradable PEM film, cells cultured on the PEM coated LC substrate, and, upon degradation of the PEM, the chemokine is released and contacted with the cells. As can be appreciated, a wide variety of agents may be incorporated into PEM films in a spatially-desired manner, including, but are not limited to, drugs, ligands, chemokines, peptides, chemical functionalities, and nutrients. PEM films also provide a stiffer interface than the interface between culture medium and liquid crystal. This stiffness been shown to affect several cell phenotypes, including spreading, adhesion, motility, and proliferation.

Therefore, in alternative methods, a step of forming a polyelectrolyte multilayer (PEM) film at the interface between the aqueous phase and liquid crystalline phase is further included. Accordingly, the protein layer comprises the PEM film.

Although a wide variety of cells may be cultured according to the present invention, living human embryonic stem cells are a particularly preferred cell type. Human embryonic stem (ES) cells, utilized in the illustrative example herein, are highly "plastic" and exceptionally susceptible to cues from their environment. Human ES cell proliferation and differentiation have both been tied to signaling pathways that are tightly connected to the cell microenvironment. For example, previous studies have shown that manipulation of the environment surrounding human ES cells by physical methods such as mechanical strain can lead to suppression of differentiation pathways.

In addition to stem cell-related applications, the present invention has utility for a variety of cell types, including corneal epithelial cells, fibroblasts, etc. The inventors have demonstrated the ability to grow fibroblasts and human embryonic stem cells on a substrate according to the invention. The inventors have passaged stem cells repeatedly and maintained them in the undifferentiated state on this substrate.

In yet another aspect, the invention provides methods for detecting cell-induced changes to a cell culture substrate by living cells. Such methods includes steps of: (a) providing a cell culture substrate by: (i) preparing an interface between an aqueous phase and a liquid crystalline phase; and (ii) depositing a protein or peptide layer at the interface; (b) seeding living cells onto the protein or peptide layer of the cell culture substrate; (c) maintaining the living cells under culture conditions; and (d) detecting reorganization of the liquid crystalline phase. The reorganization indicates cell-induced changes between the living cells and the cell culture substrate. In a particularly preferred embodiment, the living cells are human embryonic stem cells and the method provides for visualizing developmental changes occurring in the cultured cells.

In yet another aspect, the invention encompasses a liquid crystalline culture substrate upon which cells are cultured. Such a substrate includes the elements of: (a) an aqueous phase; (b) a liquid crystalline phase wherein an interface is formed between the aqueous phase and liquid crystalline phase; and (c) a protein or peptide layer positioned at the interface. As previously-described, the protein or peptide layer preferably includes at least one protein or peptide that is or may function as an extracellular matrix component such as, but not limited to, gelatin, laminin collagen, elastin, or a mixture thereof. The material available under the tradename Matrigel is a particularly preferred composition for use as the protein layer. Synthetic peptides may comprise the layer in alternative fashion or in addition to extracellular matrix components.

Although a broad variety of liquid crystalline substances may be used in practicing the invention, certain preferred embodiments utilize a liquid crystalline phase that is a liquid crystal elastomer. In certain substrates, a polyelectrolyte multilayer (PEM) film is positioned at the interface between the aqueous phase and liquid crystalline phase. Accordingly, the protein layer is comprised by the PEM film.

Substrates according to the invention may further be incorporated into devices for detecting cell-induced changes to a protein layer by living cells. These devices include: (a) a cell culture substrate having: (i) an aqueous phase; (ii) a liquid crystalline phase wherein an interface is formed between the aqueous phase and liquid crystalline phase; and (iii) a protein or peptide layer positioned at the interface; and (b) a means for imaging reorganization of the liquid crystalline phase. Reorganization indicates changes to the cell culture substrate induced by cells cultured on the cell culture substrate.

As is known to those skilled in the art, changes in optical properties of the liquid crystal can be quantified by using optical instrumentation such as, but not limited to, plate readers, cameras, scanners, photomultiplier tubes. Because the dielectric properties of liquid crystals also change with orientational order, measurements of electrical properties of liquid crystals can also be used to report changes in the interactions of molecules with liquid crystals. Thus a wide range of optical and electrical methods for transduction of cell-induced reorganization of liquid crystals is anticipated by this invention.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

The following materials and methodologies were utilized in the examples discussed in greater detail below.

Materials. The nematic liquid crystal TL205 was purchased from EMD Chemicals (Hawthorne, N.Y.) and used without further purification. Gold specimen grids (bars 20 μm thick and 55 μm wide, spaced 283 μm apart) were obtained from Electron Microscopy Sciences (Fort Washington, Pa.). The phospholipid 1,2-dilauroyl-sn-glycero-3-phosphocholine was purchased from Avanti Polar Lipids (Alabaster, Ala.) and used as received. Bovine serum albumin was purchased from Jackson ImmunoResearch Labs (West Grove, Pa.). Deionization of a distilled water source was performed with a Milli-Q system (Millipore, Bedford, Mass.) to give water with a resistivity of 18.2 M$\Omega$·cm. Glass microscope slides were Fisher's Finest Premium Grade obtained from Fisher Scientific (Pittsburgh, Pa.). Octadecyltrichlorosilane (OTS) was obtained from Fisher Scientific. 8-well chamber slides used for cell culture were purchased from Nalge Nunc International (Rochester, N.Y.). Matrigel was obtained from Invitrogen (Carlsbad, Calif.) and labeled with the succinimidyl ester, Alexa Fluor 430 carboxylic acid from Molecular Probes (Carlsbad, Calif.). The human embryonic stem cell lines H1 and H9 were derived as detailed elsewhere. J. Thomson, J. Itskovitz-Eldor, S. Shapiro, M. Waknitz, J. Swiergiel, V. Marshall, J. Jones, Science 1998, 282, 1145. ES cell medium contained 80% DMEM/F12 (Invitrogen), 20% knockout serum replacer (Invitrogen), 1% L-glutamine, and 0.1 mM MEM non-essential amino acids solution (Sigma-Aldrich, St. Louis, Mo.). ES cell medium was conditioned on mouse embryonic fibroblasts (MEFs) and supplemented with bFGF (Invitrogen). MEF medium contained 90% DMEM (Invitrogen), 10% FBS, and 1% MEM nonessential amino acids solution.

Preparation of optical cells. A detailed description of the methods used to prepare and examine the liquid crystal hosted within optical cells can be found in a previous publication. J. M. Brake, N. L. Abbott, Langmuir 2002, 16, 6101. Briefly, glass microscope slides were cleaned according to published procedures and coated with octadecyltrichlorosilane (OTS). The quality of the OTS layer was assessed by checking the alignment of 5CB confined between two OTS-treated glass slides. Any surface not causing homeotropic anchoring of 5CB was discarded. A small square of OTS-coated glass (ca. 5 mm×5 mm) was fixed to the bottom of each well of an 8-well chamber slide with epoxy and cured overnight at 60° C. The wells were rinsed several times with ethanol to remove uncured monomer and subsequently dried. Gold specimen grids that were cleaned sequentially in methylene chloride, ethanol, and methanol were placed onto the surface of the OTS-treated glass slides, one per well. Approximately 1 μL at of TL205 was dispensed onto each grid and the excess liquid crystal was removed with a syringe to produce an approximately planar interface.

Preparation of Fluorescently-labeled Matrigel. Matrigel was labeled with the epifluorescent succinimidyl ester, Alexa Fluor 430 carboxylic acid. 2 mg of frozen Matrigel was resuspended in 8 mL of 0.1 M sodium bicarbonate buffer at 4° C. 0.2 mL of the Matrigel solution was added to each well 8-well chamber slides containing TL205-impregnated grids or glass substrates. The slides were incubated at 37° C. for 2 h to allow formation of Matrigel ECM. After incubation, each well to be labeled was washed twice with 0.4 mL sodium bicarbonate buffer. 0.2 mg of Alexa Fluor 430 in 10 μL methanol was resuspended in 20 μL dimethyl sulfoxide. The resulting solution was added to 6.4 mL sodium bicarbonate buffer and 200 μL was then transferred to each well. The chamber slides were covered with foil to prevent photobleaching and incubated at room temperature for 1 h. Finally, the wells were washed 3 times in PBS to remove excess dye before cell culture.

Cell culture. Human ES cells were cultured on a Matrigel ECM using ES cell medium conditioned on MEFs, supplemented with 4 ng/mL bFGF (CM/F+). Matrigel was deposited onto TL205 or glass substrates in chamber slides as described above. ES cell colonies grown to passaging confluence (1-2×106 cells) were partially detached from their plate incubating 3-5 min in 10 mg/mL dispase at 37° C. Colonies were washed once in unconditioned ES cell medium without bFGF (UM/F−) and then gently scraped from the plate using a glass pipette. ES cell colonies were centrifuged 5 min at 1000 rpm in a Thermo IEC Centra CL2 tabletop centrifuge and resuspended in 2.5 mL CM/F+. 0.3 mL of the resuspended cells was then added to each well of the 8-well chamber slide containing TL205-impregnated grids or glass controls. The cell medium was changed daily thereafter.

Cell viability assay. Live cells were detected with the LIVE/DEAD Viability/Toxicity Kit (Molecular Probes # L-3224) following the manufacturer's protocol. Briefly, ES cells that had been cultured on TL205 substrates were rinsed 3 times with PBS and then 1 μM calcein-AM in PBS was added to each well. After 20 min, samples fluorescence microscopy was used to characterize live cells, which showed up bright due to the conversion of the non-fluorescent calcein-AM to fluorescent calcein. Cell death was not characterized with the LIVE/DEAD kit due to conflicts between the stain used for dead cells and the fluorescent tag used in Oct-4 staining, which characterized cell differentiation.

Staining of the Oct-4 transcription factor. To visualize differentiation of ES cells, cells were stained for the transcription factor Oct-4, which is expressed solely in undifferentiated ES cells. First, cells were fixed by incubating 15 min in 4% paraformaldehyde (200 mL/well) at room temperature. Next, cells were blocked using 5% milk in PBS at 4° C. for 1 h. The primary antibody, mouse anti-Oct-3/4 (Santa Cruz Biotechnology, Santa Cruz, Calif.), was diluted 1:200 in PBS+0.4% Triton X-100. 150 μL of this solution was added to each well and incubated 1 h at room temperature. Cells were then washed 5 times in PBS. The secondary antibody, Texas Red labeled goat anti-mouse (Molecular Probes) was diluted 1:500 in PBS+0.4% Triton. Cells were incubated in 150 μL of the secondary antibody solution for 1 h at room temperature. Finally, cells were washed 3 times and stored in PBS.

Flow cytometry and analysis. Following culture on TL205, cells were collected from the liquid crystal interface. Cells on the liquid crystal grids were isolated from those on the surrounding surface by placing a rubber tube with diameter approximately equal to the grid diameter on top of each grid. 0.05% trypsin/EDTA was injected into the center of the tubing and cells were incubated 10 min at 37° C., thereby dissociating only the cells growing on the TL205 and gold grid. Cells from four grids were combined to a single centrifuge tube for analysis. Trypsin was subsequently neutralized by the addition of 1 mL MEF medium, and the cells were centrifuged and washed once in FACS buffer (Ca/Mg2+-free PBS, 2% FBS, 0.1% sodium azide). A mouse anti-SSEA-4 antibody (Santa Cruz Biotechnology), which targets an ES cell marker, was diluted 1:50 in FACS buffer. Cells were resuspended in 100 μL of the primary mouse anti-SSEA-4 solution and incubated 30 min at room temperature. Cells were washed twice in FACS buffer, and incubated 390 min at room temperature in a goat anti-mouse labeled phycoerythrin solution (diluted 1:50 in FACS buffer). Samples were wrapped in foil to prevent photobleaching. Finally, samples were washed twice in FACS buffer and resuspended in a final volume of 300 μL FACS buffer for analysis. Data were collected on a FACScan flow cytometer (Beckton Dickinson, Franklin Lakes, N.J.) and analysis was performed on CellQuest (Beckton Dickinson) and WinMDI software. Cell viability was defined as whole cells (measured via light scattering) with intact membranes (measured as exclusion of the fluorescent live/dead marker propidium iodide). All whole cells excluding the live/dead marker were gated and SSEA-4 uptake was based on fluorescence levels of viable cells.

Liposome preparation. Chloroform solutions of pure DLPS or DLEPC were dispensed in a glass tube and dried under a low flow of N2 to form a thin lipid film. Residual solvent was removed under vacuum at 50° C. for several hours. The resulting lipid film was hydrated overnight at room temperature (above the lipid transition temperature) with an appropriate volume of water to yield a final lipid concentration of 100 μM. The lipid solutions appeared clear after this step, suggesting that both DLPS and DLEPC either dissolved or formed micellar aggregates in solution. Nevertheless, the lipid suspensions were sonicated for 30 min in a bath sonicator at room temperature to produce small unilamellar liposomes. Upon reconstitution the lipid solutions were clear and were used without filtering.

Polarized microscopy of the aqueous-liquid crystal interface. The orientation of TL205 within each optical cell was examined with plane-polarized light in transmission mode on an IX-71 inverted microscope with crossed polarizers. The source light intensity levels were constant for all images of the same magnification. Homeotropic alignments of the liquid crystal were determined by observing the absence of transmitted light regardless of rotation of the sample. Images were taken with a Hamamatsu camera controlled by ImagePro software.

Fluorescent microscopy. Images were obtained with an Olympus IX-71 inverted microscope. Fluorescence filter cubes with the appropriate spectral filters for each fluorophore were from Chroma Technology Corp. (Rockingham, Vt.). Images were taken with a Hamamatsu digital camera controlled by ImagePro software. The fluorescent images were taken with the liquid crystal/OTS glass interface toward the objective.

Example 1

Liquid Crystals Report the Presence and Absence of a Protein Layer in Cell Media Matrigel adsorbed to solid substrates is known to promote the adhesion and growth of human embryonic stem cells. Consequently, the inventors first sought to determine if it was possible to deposit Matrigel at the aqueous-TL205 interface and to determine the extent to which the orientational order in the liquid crystal was coupled to the presence of Matrigel. A solution of Matrigel (0.25 mg/mL, 0.1 M sodium bicarbonate) conjugated to the epifluorescent Alexa Fluor 430 label was introduced over a film of TL205 hosted in a gold grid on an OTS-coated glass slide and the Matrigel solution was allowed to gel for 1.5 h at 37° C. After exchanging the Matrigel solution with phosphate-buffered saline, fluorescence microscopy was used to image the Matrigel. Fluorescence images of Matrigel supported on TL205 that had been subjected to the above procedure showed areas of intense fluorescence on a uniformly bright background within each grid square (FIG. 1C). The speckled appearance was similar to that observed for Matrigel deposited under the same conditions on glass controls. This appearance supports the conclusion that Matrigel adsorbs at the aqueous-TL205 interface—a prerequisite for seeding of ES cells at the TL205 surface (see below).

In an effort to estimate the thickness of the Matrigel layer at the aqueous-TL205 interface, the inventors used ellipsometry to measure the thickness of Matrigel films prepared on silicon substrates treated with hydrophobic, cationic, and anionic self-assembled monolayers. In all cases, the ellipsometric thickness of nominally dry Matrigel layers was measured to be ~10 nm, suggesting that the hydrated Matrigel layers on TL205 are likely on the order of hundreds of nanometers in thickness.

After establishing the presence of Matrigel at the aqueous-TL205 interface, polarized light microscopy was used to characterize the orientational order of TL205 on which Matrigel had been deposited using the procedure described above. As a reference, the inventors examined the optical appearance of TL205 immersed in the buffer used for Matrigel deposition (no lipids, proteins, or cells present) and observed a bright optical texture with pale yellow interference colors (FIG. 1D). This appearance can be understood as follows: At the TL205-glass interface, the orientation of the liquid crystal is anchored perpendicular to the glass by the monolayer of octadecyltrichlorosilane (shown schematically in the director profile in FIG. 1A). Consequently, the bright optical appearance is the result of in-plane birefringence of the liquid crystal aligned parallel to the aqueous-TL205 interface. The presence of dark brushes emanating from points along the edges or near the center of each compartment indicates that there is a variation of the azimuthal (radial) orientation of the liquid crystal within each compartment of the grid.

The optical appearance of TL205 coated with a thin film of Matrigel at the aqueous-TL205 interface was substantially textured (FIG. 1E) as compared to the control (FIG. 1D). This appearance is distinct from the optical appearances of liquid crystals in contact with solutions of globular proteins. For example, contact of TL205 with a solution of the globular protein bovine serum albumin (BSA) yielded an optical texture that was essentially the same as that exhibited by TL205 in contact with buffer (FIG. 1F). BSA is a globular protein that likely has little long-range organization at the aqueous-TL205 interface, while Matrigel is composed primarily of laminin and collagen fibrils (~75 nm[23, 25]) and ~300 nm[26] in length, respectively) that are organized into an extended fibrous network.[26] These results suggest that the fibrillar organization of the Matrigel is reflected in the ordering of the liquid crystal TL205. This observation also suggests that the liquid crystal is able to report reorganization of Matrigel and other extracellular components by cells.

Example 2

Liquid Crystals Coated with a Protein Layer Support Cell Growth

Figure 2:
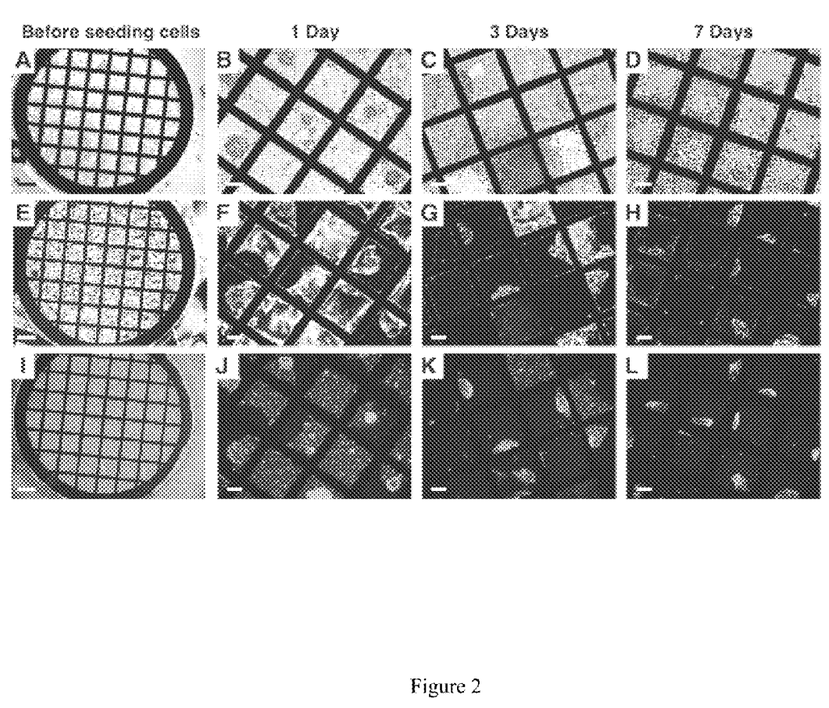
FIG. 2. Phase-contrast (A-D), polarized (E-H), and fluorescence (I-L) images of human embryonic stem cells seeded on a Matrigel-coated TL205 substrate and imaged after the times shown for each column. Scale bars are 300 µm for A, E, and I; all others are 100 µm.

Next, it was determined if it was possible to seed and grow ES cells on aqueous-TL205 interfaces that had been coated with a Matrigel film. ES cells grown to confluence were dissociated from their culture plate and added to wells containing either TL205 hosted in a gold grid or bare glass (control) at a concentration of 2.5-5.0×10⁵ cells per well. ES cells did attach and grow at Matrigel-decorated interfaces of the liquid crystal (FIG. 2). The development of the ES cell colonies was followed for up to fourteen days with phase contrast microscopy (FIG. 2A-D). After cell seeding, small colonies of ES cells were observed on the liquid crystal (FIG. 2B). Many of the colonies grew in size over the course of seven days (FIG. 2C-D), and occasionally grew to near confluence after 14 days. When ES cells were seeded directly on TL205, without a Matrigel coating, no colony attachment or growth was observed. A qualitative calcein-AM based cell viability assay indicated that the majority of stem cells on Matrigel-coated TL205 were alive after four, seven, and 12 days. Oct-4 staining, which is specific for a protein in ES cells, showed no qualitative difference in the differentiation of ES cells cultured on Matrigel-coated TL205 compared to those cultured on glass controls. Flow cytometry supported the results of both the cell viability and differentiation assays. This corresponds with qualitative data obtained by Oct-4 staining of stem cells, which indicated cells had not differentiated to a higher degree than control wells grown under standard conditions. A lower density of both initial cell colonies and the rate of radial growth of the colonies on TL205 was observed relative to controls grown on Matrigel-coated glass. Taken together, these results indicate that ES cells are able to attach to Matrigel-coated TL205 interfaces, survive for days on the TL205 interfaces, in many cases growing into large colonies similar to the colonies. The fluid nature of the underlying TL205 substrate does not appear to inhibit cell attachment or growth.

In parallel to observing the growth of ES cell colonies with phase-contrast imaging, the orientational order within the liquid crystal was followed by using polarized microscopy (in transmission mode, illuminated with white light). Changes in the orientational order of the liquid crystal as ES cell colonies attached and grew at the Matrigel-coated TL205 interface were observed (FIG. 2E-H). Initially, the Matrigel-coated TL205 appeared bright (planar anchoring at interface) with textures similar to those noted in the discussion above (FIG. 2E). After culturing stem cells for one day on Matrigel-coated TL205, the appearance of dark regions in the TL205 were observed, indicative of homeotropic anchoring of the liquid crystal. The dark regions generally appeared adjacent to the locations of ES cell colonies (compare FIGS. 2B and 2F) and grew in size as the cell colonies grew (FIG. 2G, H).

Because results suggested that the orientations of TL205 are coupled to the presence of the Matrigel deposited at the interface (FIG. 1C, 1E), it was determined if the development of regions of homeotropic anchoring was the result of reorganization of the Matrigel film by the cells. Alexa Fluor 430-labeled Matrigel was used to track the Matrigel location with fluorescence microscopy over the course of the ES cell culture (FIG. 2I-L). Initially, a speckled fluorescence on a uniformly bright background was observed (as described above), indicating a uniform coverage of the Matrigel on the liquid crystal (FIG. 2I). Following seeding of ES cells, the Matrigel fluorescence became non-uniform (FIG. 2J-L) and exhibited three distinct levels of fluorescence intensity: regions of fluorescence similar to that observed in the absence of cells, regions with increased fluorescence intensity, and regions with essentially no fluorescence. A comparison of the fluorescence images with the polarized light micrographs revealed that regions of depleted fluorescence intensity—indicative of the removal of Matrigel from the aqueous- TL205 interface—corresponded to regions of homeotropic anchoring of the TL205 (e.g., FIGS. 2J and 2F). A comparison of fluorescence and phase-contrast images showed that regions of increased fluorescence intensity corresponded to the locations of ES cell colonies (e.g., FIGS. 2J and 2B). This was particularly true at short times (1 day of culture). At longer times, the bright fluorescence typically was co-located with only portions of the large cell colonies (FIG. 2D, 2L).

These results suggest that the ES cells are exerting a force on the Matrigel film that causes the film to be removed from the areas adjacent to cell colonies. ES cell colonies also appear to condense the Matrigel to areas beneath (or, perhaps, within) the colonies. Significantly, the appearance of the liquid crystal reflects this process as a change from bright to dark (planar to homeotropic) when the Matrigel layer is removed by the cells.

Figure 3:
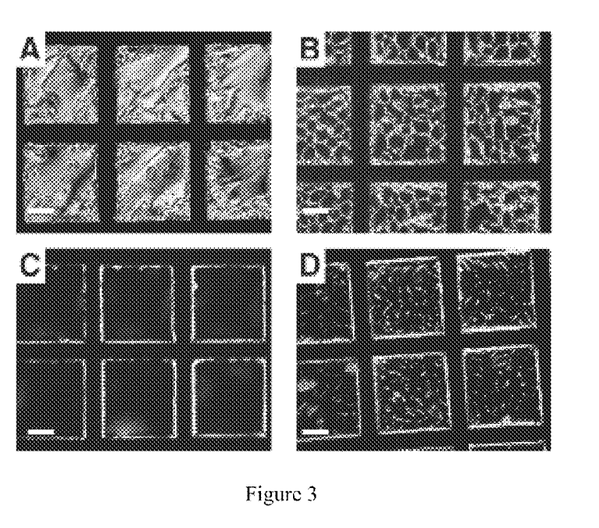

The cause of the homeotropic anchoring observed when Matrigel had been removed from the aqueous-TL205 interface was next determined. It was tested whether components of the cell medium were adsorbing to the aqueous-TL205 interface by exposing TL205 with and without a Matrigel coating to cell media for four days. The media was changed daily to simulate cell culture conditions. Following this procedure, no significant change in the optical appearance of TL205 coated with a Matrigel film was observed (FIG. 3A; compare to FIG. 1D). In contrast, TL205 lacking a Matrigel film at the aqueous-TL205 interface developed dark domains, corresponding to homeotropic anchoring of TL205 (FIG. 3B). The homeotropic domains were separated by irregular bright regions that corresponded to planar anchoring. The optical appearance is reminiscent of the anchoring of the liquid crystal 4'-pentyl-4-cyanobiphenyl (5CB) caused by phospholipids adsorbed at aqueous-5CB interfaces. To confirm that phospholipids adsorbed at aqueous-TL205 interfaces cause similar anchoring of the TL205, TL205 was exposed to an aqueous suspension of small unilamellar vesicles of 1,2-dilauroyl-sn-glycero-3-phosphocholine (DLPC). The adsorption of DLPC to the aqueous-TL205 interface led to a change in the optical appearance of TL205 from bright (planar anchoring, similar to FIG. 1B) to dark (homeotropic anchoring, FIG. 3C) within 1 h. This result is similar to that observed for the adsorption of DLPC to aqueous-5CB interfaces.

Finally, TL205 was exposed to aqueous solutions of 100 μM DLPC mixed with 1 μM BSA in an attempt to mimic the mixed nature of the cell culture medium. Initially, TL205 exhibited a bright, planar optical appearance in crossed polars. After 30 min, the optical appearance of TL205 was primarily dark (homeotropic anchoring) with thin bright regions (planar anchoring, FIG. 3D). This appearance was reminiscent of that observed for TL205 in cell media (FIG. 3B). However, the textured appearance of TL205 in contact with DLPC and BSA was not stable over time. After 1 h, the optical appearance of TL205 was completely dark (homeotropic). The fact that the mixed optical texture of TL205 was transient in DLPC/BSA mixtures, but long-lived (days) in cell medium may reflect the more complex composition of the cell medium.

These results suggest a mechanism for the connection between the appearance of the liquid crystal and the ES cell colonies growing at the Matrigel-coated TL205 interface: the homeotropic appearance of TL205 when Matrigel is removed by the cell colonies may be caused by phospholipids or proteins—perhaps products of cell breakdown—in the cell medium. The Matrigel layer appears to prevent adsorption of lipids and proteins to the aqueous-TL205 interface, thus maintaining planar anchoring of the TL205. Once the Matrigel is removed from the interface by the forces exerted by the ES cell colonies, lipids or proteins from solution are free to adsorb to the aqueous-TL205 interface, and cause a transition from planar to homeotropic anchoring of the TL205.

The results set forth herein demonstrate that it is possible to culture human embryonic stem cells on interfaces of thermotropic liquid crystals that are decorated with thin films of Matrigel. The cells survived for up to 12 days on liquid crystal substrates and showed levels of differentiation comparable to that observed for cells on glass controls. Because the orientational order of the liquid crystal was found to be coupled to the presence of the Matrigel, changes in the orientational order of the liquid crystal that can be recorded by using polarized light microscopy provides a straightforward way to image the reorganization of Matrigel by the cells. The coupling between the Matrigel and TL205 provides a simple tool for monitoring the reorganization of the Matrigel over time. Accordingly, a new approach to the culture of cells and measurements of cell-extracellular matrix interactions is provided by the present invention.

Example 3

Culture of Cells on Polyelectrolyte Multilayer (PEM)-Coated Liquid Crystals

This example demonstrates the culturing of cells on liquid crystals that are coated with PEM film. The inventors confirmed generation of PEM films on a variety of substrates (e.g., silicon chip, glass, and liquid crystal TL205) by the increased fluorescence signals from the labeled PEM component during film growth. Procedures of PEM deposition on the liquid crystal TL205 are provided below. Additional description regarding the growth of PEMs on liquid crystals can be found in the references Lockwood N A, Cadwell K D, Caruso F, et al. "Formation of polyelectrolyte multilayer films at interfaces between thermotropic liquid crystals and aqueous phases" *Advanced Materials* 18 (7): 850, 2006 and Tjipto E, Cadwell K D, Quinn J F, et al. "Tailoring the interfaces between nematic liquid crystal emulsions and aqueous phases via layer-by-layer assembly" *Nano Letters* 6 (10): 2243-2248, 1 2006, all incorporated herein by reference.

Method of Growing PEM

All steps described herein were carried out at room temperature. All polymer solutions were prepared at pH 4 (adjusted with HCl) and at 1 mg/ml for polyethylenimine (ethoxylated, Mw~70k, Sigma, USA) and hyaluronic acid (350 kDa, Genzyme, USA) solutions, and at 0.2 mg/ml for collagen (Collagen Type I, Sigma, USA) and gelatin (Sigma, USA) solutions. Polyethylenimine was used as a cationic surface charger to prepare a strongly charged surface for adsorption of weak polyelectrolytes. The ethoxylated side chains of this polyethyenimine make the polymer highly cationic.

The liquid crystal surface was pre-wetted with acetate buffer at pH 4. Collagen denatures at pH 4. The isoelectric point of hyaluronic acid is around pH 3. Thus, the PEM is built at pH 4 to preserve the collagen structure while enhancing the charges carried on the weak polyelectrolytes. There was allowed 3-5 minutes incubation for the liquid crystal to achieve homogeneous alignment in contact with the aqueous phase. This incubation time also helped the liquid crystal film stabilize following disturbance from solution addition. All solution addition or exchange was carried out with caution as the fluid turbulence could potentially dislodge liquid crystal. Polyethylenimine solution was then slowly added resulting in the gradual exchange out the buffer. Incubation was allowed for 10 minutes. The liquid crystal surface was then rinsed via solution exchange using pH 4 acetate buffer 3 times. Hyaluronic acid solution was then added using the method described for polyethylenimine solution. Incubation was again for 10 minutes. Another rinse with pH 4 acetate buffer was performed, as described earlier. Solution exchange was then carried out with collagen solution with subsequent incubation for 30 minutes. Rinses were performed before depositing subsequent bilayers of (hyaluronic acid/collagen).

For building PEM with (hyaluronic acid/gelatin) bilayers, collagen was simply substituted with gelatin solution. The procedures are substantially similar for building PEM with labeled collagen or gelatin. For building PEM on silicon or glass, the above procedure may be modified such that the substrates may be immersed (i.e., dipped) in the various solutions.

Method for Labeling Collagen or Gelatin with Alexa430 Fluorophor

Collagen or gelatin was dissolved to 1 mg/ml in 0.1M $NaHCO_3$, pH 8.3 at 37 C. Gelatin could be dissolved at higher concentrations. Meanwhile, Alexa 430-succinimidyl ester (Molecular Probes, USA) was diluted in DMSO to 10 mg/ml. While stirring, the diluted Alexa 430 solution was slowly added at protein-fluorophore ratio of 10:1 for labeling collagen and 20:1 for labeling gelatin. Incubation was at room temperature on a rocking platform for 2 hr. Labeled protein was purified by running the labeling reaction solution through Sephadex G-25 sizing column at room temperature. Proteins were eluted with pH 4 acetate buffer. A bicinchoninic acid (BCA) assay was performed to determine labeled protein concentration.

Method of NIH 3T3 Fibroblast Cell Labeling

Cell labeling was performed using freshly trypsinized cells from polystyrene culture plates. Cell suspensions of $10^5$ cells/ml were prepared in culture medium. While stirring, 0.5 vol % of DiD lipophilic tracer (Molecular Probes, USA) solution was added and incubation followed at 37 C for 15 minutes. The solution was then centrifuged at 1500 rpm for 5 minutes and cells resuspended in culture medium. The wash procedure was repeated twice.

Method of Culturing NIH 3T3 Cells on PEM-Layered TL205 Liquid Crystal Surface

Labeled 3T3 cells were utilized in this example to facilitate observation of cells on the above-described substrates. In practice, standard 8-well chamber slides were used and seeding density of $10^3$-$10^4$ cells per well was found optimal. Half of the culturing medium was exchanged every three days.

Figure 4:
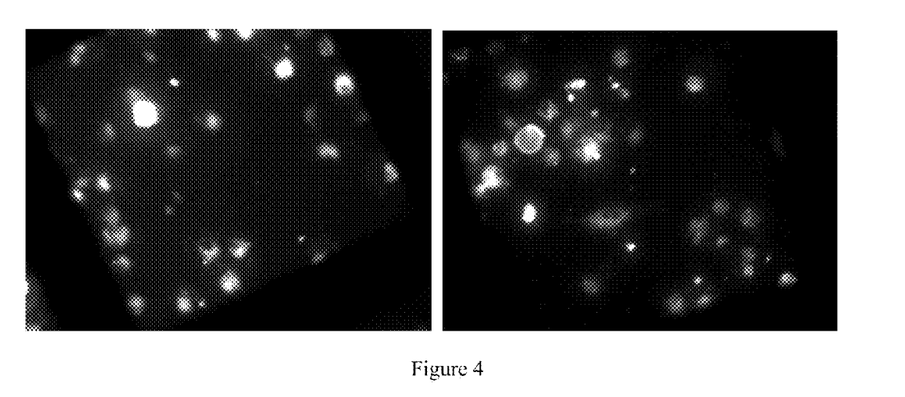
FIG. 4. DiD-labeled 3T3 cells on polyethylenimine/(hyaluronic acid/collagen)$_5$-TL205. Pictures were acquired from different wells. Images were taken 10 hours post-cell seeding.

FIG. 4 depicts DiD-labeled 3T3 cells on polyethylenimine/(hyaluronic acid/collagen)$_5$-TL205. The two panels represent pictures acquired from different wells in a standard 8-well chamber slide at 10 hours post-seeding. These results demonstrate that it is possible to culture and maintain cells on PEM coated liquid crystalline substrate.

Example 4

Culturing of Cells on Liquid Crystal Elastomer (LCE) Substrates

This example illustrates the culturing of cells on liquid crystal elastomer substrates. The LCE utilized in this example contained the mesogen M4OCH3 and polymethylhydrosiloxane, as described in the reference A. Komp and coworkers "A versatile preparation route for thin free standing liquid single crystal elastomers" *Macromol. Rapid Commun,* 26: 813-818, 2005, incorporated herein by reference.

It is preferred that the LCE sample be placed into a cell culturing compartment before any treatment is initiated to avoid future handling of the sample that might damage the sample. In this example, an LCE sample of size 1 mm×2 mm on octyltrichlorosilane (OTS)-coated glass was placed in an 8-well chamber slide. LCE was first sterilized with ethanol and then treated by soaking it in bovine calf serum for 5 days with serum exchanged every day. LCE was then conditioned in phosphate buffered saline (PBS) for 10 minutes, followed by incubation in 10 µg/ml fibronectin (Invitrogen, USA) solution at 4 C overnight. The fibronectin-coated LCE was then rinsed with PBS twice prior to cell seeding. For the 8-well chamber slide, it is preferred to exchange the medium every three days.

Results of Cell Survival and Proliferation on LCE.

Figure 5:
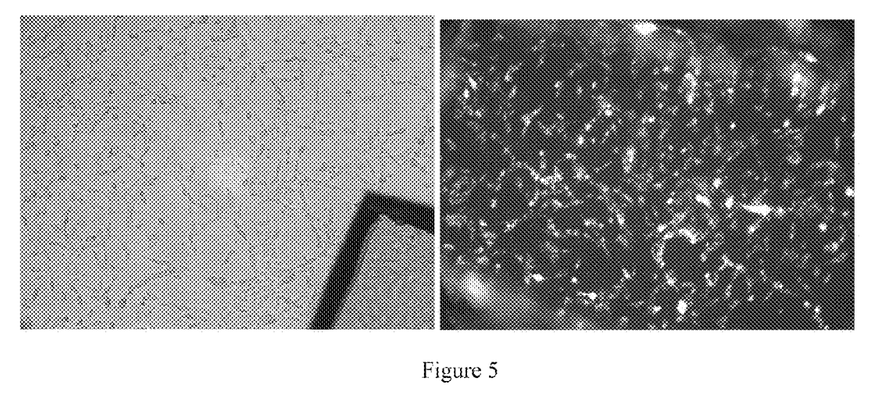
FIG. 5. NIH 3T3 cell growth on OTS-coated glass (left panel, phase contrast image) and LCE (right panel, fluorescent image of Di-D treated cells) in a well treated with bovine calf serum. Images were taken 12 hours post-cell seeding.

Cell growth was observed on both glass (control) and on LCE. FIG. 5 illustrates that the two materials were comparable in terms of cell density at 12 hour post-cell seeding. NIH 3T3 cell grown on OTS-coated glass are shown in a phase contrast image in the left panel of FIG. 5. NIH 3T3 cells grown on the above-described LCE are shown the fluorescent image (right panel) of labeled cells in a well treated with bovine calf serum.

Fibroblasts typically require 4-6 hrs to fully spread on polystyrene culture plates following standard passage protocols. A twelve hour window for cell attachment allowed sufficient time for cells to spread and grow on LCE.

Figure 6:
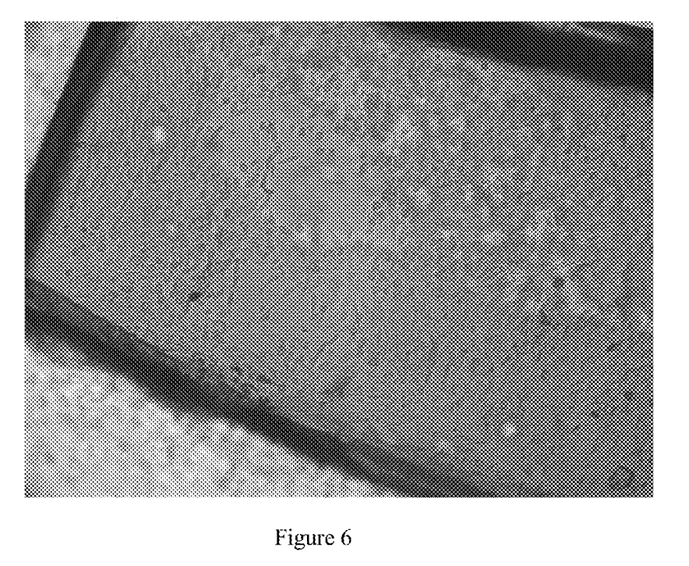
FIG. 6 NIH 3T3 cell growth on serum-treated LCE (the same sample depicted in the right panel of FIG. 5). The image was taken on the 5$^{th}$ day post-cell seeding.

FIG. 6 provides an image of cells on serum-treated LCE on the $5^{th}$ day post-cell seeding. The sample shown is that same LCE substrate surface that was shown in the comparative FIG. 5.

The results provided in this example demonstrate that cells attach, spread and proliferate on LCE substrates.

Those skilled in the art will recognize, or be able to ascertain using no more than routine experimentation, numerous equivalents to the specific materials and methods described herein. Such equivalents are considered to be within the scope of this invention and encompassed by the following claims.

What is claimed is:

1. A cell culture substrate upon which cells are cultured, comprising:
   (a) an aqueous phase;
   (b) a liquid crystalline phase wherein an interface is formed between the aqueous phase and liquid crystalline phase; and
   (c) a protein or peptide layer positioned at the interface, wherein the protein or peptide layer is an extracellular matrix component.

2. The cell culture substrate according to claim 1 wherein the protein or peptide layer comprises gelatin, laminin, collagen, elastin, or mixtures thereof.

3. The cell culture substrate according to claim 1 wherein said protein or peptide layer comprises a synthetic polypeptide.

4. The cell culture substrate according to claim 1 wherein the liquid crystalline phase is a liquid crystal elastomer.

5. The cell culture substrate according to claim 1, wherein the interface comprises a polyelectrolyte multilayer (PEM) film incorporating the protein or peptide layer.

* * * * *